United States Patent
Stam et al.

(10) Patent No.: US 11,457,583 B2
(45) Date of Patent: Oct. 4, 2022

(54) *SEPTORIA* RESISTANCE IN CELERY

(71) Applicant: Bejo Zaden B.V., Warmenhuizen (NL)

(72) Inventors: Elisabeth Lucia Maria Stam, Heerhugowaard (NL); Jacob van Dorp, Nieuwe Niedorp (NL); Albertus Johannes Maria Schrijver, Warmenhuizen (NL)

(73) Assignee: Bejo Zaden B.V., Warmenhuizen (NL)

( * ) Notice: Subject to any disclaimer, the term of this patent is extended or adjusted under 35 U.S.C. 154(b) by 0 days.

(21) Appl. No.: 16/487,461

(22) PCT Filed: Mar. 2, 2018

(86) PCT No.: PCT/EP2018/055155
§ 371 (c)(1),
(2) Date: Aug. 21, 2019

(87) PCT Pub. No.: WO2018/158417
PCT Pub. Date: Sep. 7, 2018

(65) Prior Publication Data
US 2019/0364777 A1 Dec. 5, 2019

(30) Foreign Application Priority Data
Mar. 2, 2017 (NL) ..................................... 2018464

(51) Int. Cl.
| | | |
|---|---|---|
| *A01H 6/06* | (2018.01) | |
| *A01H 5/04* | (2018.01) | |
| *C07K 14/415* | (2006.01) | |
| *C12Q 1/6895* | (2018.01) | |
| *A01H 5/06* | (2018.01) | |
| *A01H 1/04* | (2006.01) | |

(52) U.S. Cl.
CPC ............... *A01H 6/064* (2018.05); *A01H 1/04* (2013.01); *A01H 5/04* (2013.01); *A01H 5/06* (2013.01); *C07K 14/415* (2013.01); *C12Q 1/6895* (2013.01); *C12Q 2600/13* (2013.01); *C12Q 2600/158* (2013.01)

(58) Field of Classification Search
None
See application file for complete search history.

(56) References Cited

U.S. PATENT DOCUMENTS
2018/0116145 A1 5/2018 Deneer

FOREIGN PATENT DOCUMENTS
WO 2017005669 A1 1/2017

OTHER PUBLICATIONS

Zhu et al. Overview of studies on celery late blight disease. (2011) China Vegetables; No. 14; pp. 1-8 (Year: 2011).*
Definition of "as" (2022) downloaded on Feb. 24, 2022 from http://meriam-webster.com/dictionary/as; p. 1; definition inserted into office action, (Year: 2022).*
Edwards et al., "The response of different celery genotypes to infection by Septoria apiicola", Plant Pathology, 1997, pp. 264-270, vol. 46.
Evenor et al., "Somaclonal variation in celery and selection by coculturing toward resistance to Septoria apiicola", Plant Cell, Tissue and Organ Culture, 1994, pp. 203-210, vol. 39:3.
Honma et al., "Hybridization Between Pascal Celery and Parsley", Euphytica, 1980, pp. 801-805, vol. 29.
Muminovic et al., Abstract for "Prospects for celeriac (*Apium graveolens* var. *rapaceum*) improvement by using genetic resources of Apium, as determined by AFLP markers and morphological characterization", Plant Genetic Resources Characterization and Utilization, Dec. 2004, pp. 189-198, vol. 2:3.
Ochoa et al., "Apium Wild Species: Novel Sources for Resistance to Late Blight in Celery", Plant Breeding, 1989, pp. 317-321, vol. 102.

* cited by examiner

Primary Examiner — Cathy Kingdon Worley
(74) Attorney, Agent, or Firm — The Webb Law Firm

(57) ABSTRACT

The present invention relates to *Apium graveolens* plants being resistant to one or more genomically encoded resistances to the plant pathogen *Septoria apiicola*. Specifically the present invention relates to *Apium graveolens* plants wherein at least one genomically encoded resistance to the plant pathogen *Septoria apiicola* is the genomically encoded resistance to the plant pathogen *Septoria apiicola* as present in deposit NCIMB 42711. The present invention further relates to hybrids containing the present *Septoria apiicola* resistance and agents, as molecular markers, suitable for detecting the present invention.

Figure 1:

3 Claims, 3 Drawing Sheets
Specification includes a Sequence Listing.

SEQUENCE LISTING

<160> NUMBER OF SEQ ID NOS: 26

<210> SEQ ID NO 1
<211> LENGTH: 51
<212> TYPE: DNA
<213> ORGANISM: Apium graveolens

<400> SEQUENCE: 1
cgaacccgaa acctaaagct caacaaccac cagtgccaat gccaccatca c    51

<210> SEQ ID NO 2
<211> LENGTH: 51
<212> TYPE: DNA
<213> ORGANISM: Apium graveolens

<400> SEQUENCE: 2
cgaacccgaa acctaaagct caacaaacac cagtgccaat gccaccatca c    51

<210> SEQ ID NO 3
<211> LENGTH: 51
<212> TYPE: DNA
<213> ORGANISM: Apium graveolens

<400> SEQUENCE: 3
cttcctttca gttgagctgg atacaatagc atctggatta accacaccaa c    51

<210> SEQ ID NO 4
<211> LENGTH: 51
<212> TYPE: DNA
<213> ORGANISM: Apium graveolens

<400> SEQUENCE: 4
cttcctttca gttgagctgg atacaagagc atctggatta accacaccaa c    51

<210> SEQ ID NO 5
<211> LENGTH: 51
<212> TYPE: DNA
<213> ORGANISM: Apium graveolens

<400> SEQUENCE: 5 taaaaaaga aaagaagag gaacaacaac acacaattct atcattaaac t    51

<210> SEQ ID NO 6
<211> LENGTH: 51
<212> TYPE: DNA
<213> ORGANISM: Apium graveolens

<400> SEQUENCE: 6 taaaaaaga aaagaagag gaacaataac acacaattct atcattaaac t    51

<210> SEQ ID NO 7
<211> LENGTH: 51
<212> TYPE: DNA
<213> ORGANISM: Apium graveolens

<400> SEQUENCE: 7
aatgatcaat cgtaggttgt attgcttgaa catgccctta catgcataga a    51

<210> SEQ ID NO 8
<211> LENGTH: 51
<212> TYPE: DNA
<213> ORGANISM: Apium graveolens

<400> SEQUENCE: 8
aatgatcaat cgtaggttgt attgctcgaa catgccctta catgcataga a    51

<210> SEQ ID NO 9
<211> LENGTH: 51
<212> TYPE: DNA
<213> ORGANISM: Apium graveolens

```
<400> SEQUENCE: 9
cgaacctcct ctaaactctc tccgcctatc ccaacaaccc caacaaactc c        51

<210> SEQ ID NO 10
<211> LENGTH: 51
<212> TYPE: DNA
<213> ORGANISM: Apium graveolens

<400> SEQUENCE: 10
cgaacctcct ctaaactctc tccgccaatc ccaacaaccc caacaaactc c        51

<210> SEQ ID NO 11
<211> LENGTH: 51
<212> TYPE: DNA
<213> ORGANISM: Apium graveolens

<400> SEQUENCE: 11
gctgtagcac tgatactaca ccatcaggct cttgatakag agagttcttt g        51

<210> SEQ ID NO 12
<211> LENGTH: 51
<212> TYPE: DNA
<213> ORGANISM: Apium graveolens

<400> SEQUENCE: 12
gctgtagcac tgatactaca ccatcatgct cttgatakag agagttcttt g        51

<210> SEQ ID NO 13
<211> LENGTH: 51
<212> TYPE: DNA
<213> ORGANISM: Apium graveolens

<400> SEQUENCE: 13
tccattcttc cacttctcaa caatgccgga tcaagtttct ctacatgatt a        51

<210> SEQ ID NO 14
<211> LENGTH: 51
<212> TYPE: DNA
<213> ORGANISM: Apium graveolens

<400> SEQUENCE: 14
tccattcttc cacttctcaa caatgcagga tcaagtttct ctacatgatt a        51

<210> SEQ ID NO 15
<211> LENGTH: 51
<212> TYPE: DNA
<213> ORGANISM: Apium graveolens

<400> SEQUENCE: 15
gatattgggt cagggtgaga acaagctagc ccaaccagta acactctcct c        51

<210> SEQ ID NO 16
<211> LENGTH: 51
<212> TYPE: DNA
<213> ORGANISM: Apium graveolens

<400> SEQUENCE: 16
gatattgggt cagggtgaga acaagccagc ccaaccagta acactctcct c        51

<210> SEQ ID NO 17
<211> LENGTH: 51
<212> TYPE: DNA
<213> ORGANISM: Apium graveolens
```

<400> SEQUENCE: 17
agttctagcc tgctacttgc tactctgcta ctcagaagca gaggcgtccg a      51

<210> SEQ ID NO 18
<211> LENGTH: 51
<212> TYPE: DNA
<213> ORGANISM: Apium graveolens

<400> SEQUENCE: 18
agttctagcc tgctacttgc tactctccta ctcagaagca gaggcgtccg a      51

<210> SEQ ID NO 19
<211> LENGTH: 51
<212> TYPE: DNA
<213> ORGANISM: Apium graveolens

<400> SEQUENCE: 19
gatttttgag ctaaaagaat tgctgtttgt ttgagatgtt acatacaaaa a      51

<210> SEQ ID NO 20
<211> LENGTH: 51
<212> TYPE: DNA
<213> ORGANISM: Apium graveolens

<400> SEQUENCE: 20
gatttttgag ctaaaagaat tgctgtctgt ttgagatgtt acatacaaaa a      51

<210> SEQ ID NO 21
<211> LENGTH: 51
<212> TYPE: DNA
<213> ORGANISM: Apium graveolens

<400> SEQUENCE: 21
tgcatccatt agcaacgaca accctgcgct agtttcatgt gttgatgatg a      51

<210> SEQ ID NO 22
<211> LENGTH: 51
<212> TYPE: DNA
<213> ORGANISM: Apium graveolens

<400> SEQUENCE: 22
tgcatccatt agcaacgaca accctgtgct agtttcatgt gttgatgatg a      51

<210> SEQ ID NO 23
<211> LENGTH: 51
<212> TYPE: DNA
<213> ORGANISM: Apium graveolens

<400> SEQUENCE: 23
atttctccat acagatggca ttcttttgag ttgatamtat acagtgcagc c      51

<210> SEQ ID NO 24
<211> LENGTH: 51
<212> TYPE: DNA
<213> ORGANISM: Apium graveolens

<400> SEQUENCE: 24
atttctccat acagatggca ttctttcgag ttgatamtat acagtgcagc c      51

<210> SEQ ID NO 25
<211> LENGTH: 51
<212> TYPE: DNA
<213> ORGANISM: Apium graveolens

```
<400> SEQUENCE: 25
aaaggttatc gtcaagtact tcaaatgttt cctctcttga caaaaagaty a        51

<210> SEQ ID NO 26
<211> LENGTH: 51
<212> TYPE: DNA
<213> ORGANISM: Apium graveolens

<400> SEQUENCE: 26
aaaggttatc gtcaagtact tcaaatctttt cctctcttga caaaaagaty a       51
```

SEPTORIA RESISTANCE IN CELERY

CROSS-REFERENCE TO RELATED APPLICATIONS

This application is the United States national phase of International Application No. PCT/EP2018/055155 filed Mar. 2, 2018, and claims priority to Dutch Patent Application No. 2018464 filed Mar. 2, 2017, the disclosures of which are hereby incorporated by reference in their entirety.

The Sequence Listing associated with this application is filed in electronic format via EFS-Web and is hereby incorporated by reference into the specification in its entirety. The name of the text file containing the Sequence Listing is 1906407_ST25.txt. The size of the text file is 4,204 bytes, and the text file was created on Aug. 19, 2019.

The present invention relates to *Apium graveolens* plants being resistant to the plant pathogen *Septoria apiicola*. The present invention further relates to hybrid celery or celeriac plants being resistant to the plant pathogen *Septoria apiicola* and to molecular markers suitable for detecting the present *Septoria apiicola* resistance.

Celery (*Apium graveolens*) and celeriac (*Apium graveolens* var. *rapaceum*) both are members of the *Umbelliferae*, a family of aromatic flowering plants together with carrot, parsnip, parsley and e.g. coriander, fennel and dill. Many members of this family are cultivated for their leaves, petioles, hypocotyl bulbs, taproots or seeds; in some cases compounds with supposed health promoting effects like apiin and apigenin can be extracted from celery and parsley plants or seeds. Celery seed is used as a spice; its extracts are used in medicines.

The seeds can be ground and mixed with salt, to produce celery salt. Celery salt can also be made from an extract of the roots or using dried leaves. Celery salt is used as a seasoning.

Lunularin is a dihydrostilbenoid found in common celery. Some aromatic compounds of celery leaves and stalks are reported as butylphthalide and sedanolide which are primarily responsible for the taste and aroma of celery.

Celery has a very long history of cultivation, the first written mention of the crop stems from 1664 and Linnaeus described the plant in his *Species Plantarum* in 1753.

The family *Umbelliferae* was named after their characteristic inflorescence, a simple or compound umbel (a number of short flower stalks growing from a common point). Flowers in this umbel are in general creamy white, and about 3 mm in diameter. Seeds produced are roughly ovoid and in general 1.5-2 mm long.

The wild celery known as "smallage" can be as high as 1 meter; it has a furrowed stalk with wedge shaped leaves; the whole plant has a strong, earthy taste and a distinctive smell. From the cultivated forms, celery and celeriac, leaves, leaf stalks and taproot are used in salads (leaves, stalks) and stews and soups (bulbs from celeriac). Stalks can easily be separated into strings of vascular bundles.

Breeding developed modern cultivars which were selected, amongst others for solid petioles and large leaves. These leaves are featherlike (pinnate, bipinnate) from 3-6 cm long and 2-4 cm broad.

With cultivation and blanching, the stalks lose their acidic properties and assume the mild, sweetish and aromatic taste typical for celery as a salad plant.

Next to these useful properties, surprisingly celery and celeriac are also plants which might provoke allergic reactions; the allergen is present in all parts and most abundantly in the seeds. Cooking does not destroy the allergen; even an allergenic reaction can be triggered by consuming food that has been processed with machines that previously processed celery. Therefore in the European Union, foods that contain or may contain (traces of) celery must be clearly labeled as such.

Bergapten, a furocoumarin, in the seeds can increase photosensitivity, so the use of essential oil externally in bright sunshine should be avoided.

Three main types of celery are known for cultivation: celery for cutting leaves and using leaf stalks (*A. graveolens* var. *secalinum*), blanched celery (var. *dulce*) where petioles are harvested (blanched by treatment or as character of the crop) and celeriac (var. *rapaceum*) from which the bulb or tuber (more correct, a thickened hypocotyl) is harvested. All varieties are used for soups and/or stews.

For cultivation, celery plants are grown from seed, sown either in a hot bed or in the open garden according to the season of the year, and they are, on attaining a height of 15-20 cm, planted out in deep trenches for convenience of blanching, which is effected by earthing up to exclude light from the stems. However, modern cultivars have leaves/stalks that also blanch without this laborious treatment.

Celeriac (incorrectly named celery root) forms a large bulb from its hypocotyl which is white on the inside. This bulb can be stored for months and serves as a main ingredient for stews and soups. Also from celeriac leaves are used as seasoning.

Due to the very high uniformity which modern cultivars possess, fields are only harvested once. After removing leaves and stalks, celery can be stored for several weeks at temperatures between 0 to 2° C.

Celery is eaten around the world as a vegetable. In North America the crisp petiole (leaf stalk) is used. In Europe celeriac, the hypocotyl, is used as a root vegetable. The leaves are strongly flavored and are used less often, either as a flavoring in soups and stews or as a dried herb.

As with many cultivated crops, also *Apium graveolens* is challenged by several pathogens. Next to viruses and several insects as leaf miners and shield bugs like *Graphosoma* sp., the most important pathogen threatening celery and celeriac cultivation is celery leaf spot or late blight, caused by the Ascomycete fungus *Septoria apiicola*.

Spores from *S. apiicola* are deposited on the plant by splashing or by movement of spores by contact. Infection of the host plant is promoted by cool and wet weather conditions. Temperatures below 24° C. combined with a high humidity allow for a great production of spores which then easily spread further in the crop. *Septoria* produces large amounts of asexual spores in fruiting bodies called pycnidia. Also, *Septoria* is seed borne and fruiting bodies can be found on the seed coat of celery seeds.

Thus, first appearance of the disease can already be noticed on the seedbed. Spores that are splashed onto healthy leaves germinate when moisture is available and produce initially a fungal thread called germ tube. This tube grows on the epidermis of the plant and then enters the leaf. Internally, the fungus keeps proliferating, causing yellow and then brown spots on the host. These leaf spots render a crop which unsuitable for sales, even when it is a minor affection of the leaf and/or the stalk. By severe infections also total yield and storability of the crop are affected. This holds especially for celery rather than celeriac since on this part of the plant no symptoms are developed. However, an infection with *Septoria* can also lead to loss of yield of celeriac.

It is therefore a desire to provide *Apium graveolens* plants with an improved tolerance or resistance to *Septoria apii-* cola, the causal agent of leaf spot or late blight. When *Apium graveolens* plants with an improved tolerance or resistance to *Septoria apiicola* are available, several advantages can be achieved. Yield and quality of the crop improve and a reduction in the application of fungicides can be reached.

One interesting approach was performed two decades ago, when researchers applied the process of somaclonal variation and selection to develop resistant cells, and consequently resistant plants. As described in ref. 1, authors used an isolate of *S. apiicola* to select *A. graveolens* cells by co-culturing cells on solid medium or in the fungal culture filtrate from the fungus. Resistant cells were developed, presumably by somaclonal variation, that were not killed off by the toxic compounds secreted by the fungus.

When plants were regenerated from these cells, they showed a range of different degrees of tolerance to *S. apiicola* in greenhouse tests. Plants yielded tolerant progenies but there are to our knowledge, no varieties on the market with an improved tolerance to *S. apiicola* originating from this or similar research.

To develop a solution for this problem, a breeding program was developed where first a source of resistance was identified. During several years, this source plant was crossed, backcrossed and finally self-pollinated to develop a parent line.

Considering the above, it is an object of the present invention, amongst other objects to obviate the above problems in the prior art.

This object, amongst other objects, is achieved by the present invention through the plants outlined in the appended claims.

Specifically, this object, amongst other objects, is achieved by providing an *Apium graveolens* plant, preferably cytoplasmic male sterile, which plant comprises one or more genomically encoded resistances against the plant pathogen *Septoria apiicola*.

According a preferred embodiment the present at least one genomically encoded resistance against the plant pathogen *Septoria apiicola* is the genomically encoded resistance against the plant pathogen *Septoria apiicola* as present in deposit NCIMB 42711 (National Collections of Industrial, Food and Marine Bacteria (NCIMB), NCIMB Limited, Ferguson Building; Craibstone Estate, Bucksburn Aberdeen, Scotland, AB21 9YA United Kingdom) deposited on Jan. 6, 2017.

According to another preferred embodiment, the present at least one genomically encoded resistance against the plant pathogen *Septoria apiicola* is obtained, or derived, from deposit NCIMB 42711.

The present *Apium graveolens* plants preferably comprise in their genome at least one sequence selected from the group consisting of SEQ ID No. 1, SEQ ID No. 3, SEQ ID No. 5, SEQ ID No. 7, SEQ ID No. 9, SEQ ID No. 11, SEQ ID No. 13, SEQ ID No. 15 and SEQ ID No. 17. The present sequences represent the resistance providing allele while plants comprising in their genome at least one sequence selected from the group consisting of SEQ ID No. 2, SEQ ID No. 4, SEQ ID No. 6, SEQ ID No. 8, SEQ ID No. 10, SEQ ID No. 12, SEQ ID No. 14, SEQ ID No. 16 and SEQ ID No. 18 comprise the susceptible allele.

The present *Apium graveolens* plants further preferably comprise in their genome at least one sequence selected from the group consisting of SEQ ID No. 19, SEQ ID No. 21, SEQ ID No. 23 and SEQ ID No. 25. The present sequences represent the resistance providing allele while plants comprising in their genome at least one sequence selected from the group consisting of SEQ ID No. 20, SEQ ID No. 22, SEQ ID No. 24 and SEQ ID No. 26 comprise the susceptible allele.

The present *Apium graveolens* plants more preferably comprise in their genome at least one sequence selected from the group consisting of SEQ ID No. 1, SEQ ID No. 3, SEQ ID No. 5, SEQ ID No. 7, SEQ ID No. 9, SEQ ID No. 11, SEQ ID No. 13, SEQ ID No. 15 and SEQ ID No. 17 and at least one sequence selected from the group consisting of SEQ ID No. 19, SEQ ID No. 21, SEQ ID No. 23 and SEQ ID No. 25. The present sequences represent the resistance providing alleles while plants comprising in their genome at least one sequence selected from the group consisting of SEQ ID No. 2, SEQ ID No. 4, SEQ ID No. 6, SEQ ID No. 8, SEQ ID No. 10, SEQ ID No. 12, SEQ ID No. 14, SEQ ID No. 16 and SEQ ID No. 18 and at least one sequence selected from the group consisting of SEQ ID No. 20, SEQ ID No. 22, SEQ ID No. 24 and SEQ ID No. 26 comprise susceptible alleles.

Preferably, the present at least one sequences are at least two, at least three, at least four, at least five, at least six, at least seven, at least eight or nine of SEQ ID No. 1, SEQ ID No. 3, SEQ ID No. 5, SEQ ID No. 7, SEQ ID No. 9, SEQ ID No. 11, SEQ ID No. 13, SEQ ID No. 15 and SEQ ID No. 17 and two, at least three or four of SEQ ID No. 19, SEQ ID No. 21, SEQ ID No. 23 and SEQ ID No. 25.

According to an especially preferred embodiment, the present plant is selected from the group consisting of *A. graveolens* var. *secalinum*, *A. graveolens* var. *dulce*, and *Apium graveolens* var. *rapaceum*.

The present invention also relates to hybrid celery or celeriac obtainable by crossing *Septoria apiicola* susceptible celery or celeriac with the present *Apium graveolens* plants or hybrid celery or celeriac obtainable by crossing a *Septoria apiicola* susceptible celery or celeriac with deposit NCIMB 42711.

The present invention further relates to a method for identifying a genomically encoded resistance against the plant pathogen *Septoria apiicola* as present in deposit NCIMB 42711, the method comprises the step of detecting the genomically encoded resistance using one or more molecular markers.

The present invention further also relates to seeds or plant parts of plants defined above or to seeds capable of providing the present plants and to molecular markers which markers co-segregate with a genomically encoded resistance against the plant pathogen *Septoria apiicola* as present in deposit NCIMB 42711.

The present invention furthermore relates to molecular markers which markers co-segregate with a genomically encoded resistance against the plant pathogen *Septoria apiicola* as present in deposit NCIMB 42711 which molecular markers are selected from the group consisting of SEQ ID No. 1, SEQ ID No. 3, SEQ ID No. 5, SEQ ID No. 7, SEQ ID No. 9, SEQ ID No. 11, SEQ ID No. 13, SEQ ID No. 15, SEQ ID No. 17, SEQ ID No. 19, SEQ ID No. 21, SEQ ID No. 23 and SEQ ID No. 25.

FIGURES

Figure 2:
Figure 3:

FIGS. 1 to 3: show photographs of representative plants according to the present invention.
These photographs were taken on one test location with natural infection with *Septoria apiicola*.
Specifically, FIG. 1 shows an overview of material grown from the deposit seeds, with affected susceptible plants in the background, FIG. 2 shows healthy unaffected leaf stalks of material grown from the deposit seeds and FIG. 3 shows healthy, unaffected leaves of material grown from the deposit seeds.

EXAMPLES

Example 1

General Protocol for Assessing Resistance

The pathogen *Septoria apiicola* is kept on dry, infected leaves at 4° C. To prepare an inoculum, a layer of leaves of about 3-4 cm thick is put on filter paper in a plastic container of 21*15*2.5 cm; these leaves are wetted by spraying water until they are completely wet (not soaked). These containers are closed and put under light for three days; after this period leaves are washed with 0.5 liter of water. Spore concentration is not determined since *Septoria apiicola* spores are too small; the presence of the spores is only confirmed by microscopy. The inoculum can be used directly but can be stored for up to 6 hours at 4° C.

Per genotype to be tested, 40 plants were assessed in two replicates. As susceptible control varieties Tango and/or Golden Spartan were used. For tests in the Netherlands, seeds were sown at the end of May or beginning of June; emerged plants are grown further in the field with a distance of 50*20 cm for celery or 50*35 cm for celeriac.

Inoculation is performed from the beginning of August; depending on conditions this inoculation has to be repeated, preferably under wet or drizzling conditions. To inoculate, infected leaves are spread in the crop or the spore suspension is dispersed using an ultra-low volume or droplet sprayer.

Tests in other parts of the world can also be performed provided the inoculation is done under circumstances with high relative humidity and moderate temperatures.

To assess the level of damage to the leaves, a score is made on a scale of 0 (completely affected) to 9 (no symptoms). When the plant stands longer, symptoms increase.

Damage is scored visually for leaves and stalks. For both celery and celeriac, a crop without any symptoms on leaves and/or leafstalks is highly preferred.

Example 2

As Second Example is Described how Disease Resistance is Assessed Under Field Circumstances in Guatemala In contrast to the Netherlands, the test location is on an altitude of 1300-1500 meters above sea level. This temperate area is characterized by a wet season (from mid-May until the end of October) where there is enough rainfall (total about 1100 mm) and, due to the low temperatures at night, relative humidity is high. Daytime temperature ranges from 15 to 25° C.; night temperature from 9 to 14° C. During the rainy season, this results every night in a long wet leaf period (WLP) which is important for development of *S. apiicola* on the crop. These favorable conditions are very predictable resulting in good annual disease tests.

Example 3

Results of Assessment for Resistance Against *Septoria apiicola*

| Cultivar | Score for S.a. in NL Inoculated test | Score for S.a. in GT Natural infection |
|---|---|---|
| Any susceptible variety (e.g. Tango, Golden Spartan) | 1-2 | 1-2 |
| Deposit NCIMB 42711 | 6 | 6-8 |

The assessment of resistance is scored on a scale from 0 to 9, where 0 is completely susceptible and 9 is high resistant.

Example 4

Production of F1 Seed Applying CMS

One of the requisites for a modern hybrid variety is that inbreeding, resulting in off type plants, is minimized. In celery, a reliable system for hybrid production is available based on cytoplasmic male sterility. Applying this feature for seed production with male and female parent lines, hybrids essentially are resulting 100% from pure cross pollinations.

Example 5

Genomically Encoded Resistance Against *Septoria apiicola* in *Apium graveolens* Plant The genomic analysis of the *Septoria apiicola* resistant *Apium graveolens* plants has shown QTLs on linkage group 1 (LG1) and/or linkage group 9 (LG9). These QTLs are defined by the SNP markers listed in the table below.

| SEQ ID No. | Genetic position (linkage group, cM) | Sequence (SNP nucleotide is highlighted bold and underlined, first nucleotide is of the resistant allele and second of the susceptible one) |
|---|---|---|
| SEQ ID No. 1/2 | LG01, 59.195 | CGAACCCGAAACCTAAAGCTCAACAA[C/A]CACCAGTGCCAATGCCACCATCAC |
| SEQ ID No. 3/4 | LG01, 60.618 | CTTCCTTTCAGTTGAGCTGGATACAA[T/G]AGCATCTGGATTAACCACACCAAC |
| SEQ ID No. 5/6 | LG01, 60.861 | TAAAAAAAGAAAAAGAAGAGGAACAA[C/T]AACACACAATTCTATCATTAAACT |
| SEQ ID No. 7/8 | LG01, 61.580 | AATGATCAATCGTAGGTTGTATTGCT[T/C]GAACATGCCCTTACATGCATAGAA |
| SEQ ID No. 9/10 | LG01, 61.892 | CGAACCTCCTCTAAACTCTCTCCGCC[T/A]ATCCCAACAACCCCAACAAACTCC |
| SEQ ID No. 11/12 | LG01, 62.187 | GCTGTAGCACTGATACTACACCATCA[G/T]GCTCTTGATAKAGAGAGTTCTTTG |

| SEQ ID No. | Genetic position (linkage group, cM) | Sequence (SNP nucleotide is highlighted bold and underlined, first nucleotide is of the resistant allele and second of the susceptible one) |
|---|---|---|
| SEQ ID No. 13/14 | LG01, 62.187 | TCCATTCTTCCACTTCTCAACAATGC[C/A]GGATCAAGTTTCTCTACATGATTA |
| SEQ ID No. 15/16 | LG01, 62.501 | GATATTGGGTCAGGGTGAGAACAAGC[T/C]AGCCCAACCAGTAACACTCTCCTC |
| SEQ ID No. 17/18 | LG01, 63.110 | AGTTCTAGCCTGCTACTTGCTACTCT[G/C]CTACTCAGAAGCAGAGGCGTCCGA |
| SEQ ID No. 19/20 | LG09, 112.525 | GATTTTTGAGCTAAAAGAATTGCTGT[T/C]TGTTTGAGATGTTACATACAAAAA |
| SEQ ID No. 21/22 | LG09, 113.396 | TGCATCCATTAGCAACGACAACCCTG[C/T]GCTAGTTTCATGTGTTGATGATGA |
| SEQ ID No. 23/24 | LG09, 115.647 | ATTTCTCCATACAGATGGCATTCTTT[T/C]GAGTTGATAMTATACAGTGCAGCC |
| SEQ ID No. 25/26 | LG09, 116.512 | AAAGGTTATCGTCAAGTACTTCAAAT[G/C]TTTCCTCTCTTGACAAAAAGATYA |

Example of Pedigree, Leading to the Described Hybrid with High Level of Resistance to *Septoria Apiicola*

In intermediate years plants were field-tested for their level of resistance.

| Year | Parent 1 | Parent 2 | Harvested as | Seedlot # | |
|---|---|---|---|---|---|
| 1987 | Blevo | Afina | J7071 | | 5 plants for selfing |
| 1995 | J7071-M | | V6747 | | =new backcross with source (mix of plants) |
| 1987 | Blevo | Afina | J7071 | | |
| 1989 | J7071-M selfed | n.a. | L5987 | | |
| 1990 | Summit | L5687-2 | P6 | | |
| 1992 | P6-6 selfed | n.a. | R6352 | | |
| 1995 | SumSepBlev | R6352-7 | V6729 | | |
| 1998 | V6747 | V6729 | Y6779 | | |
| 2000 | Y6779-18 selfed | n.a. | A15898 | | |
| 2002 | A30599 | A15898-6 | E16504 | | |
| 2004 | E16504 F2 | n.a. | G1209 | | |
| 2005 | G46052 | G1209 | K50419 | | |
| 2008 | K50419 F1 | n.a. | N5092 | 087137 | testcross made |
| 2010 | N5092-2 selfed | n.a. | R16157 | | |
| 2014 | S444 (=N5092-2) | n.a. | | | S444-3 renamed Gisep28 |
| 2015 | S444-3 | | | | Retest in the field; fixed parentline |
| 2016 | PremA3-2 | Gisep28-1 | | 1520725 | Hybrid, deposit |

Deposit Information

A sample of *A. graveolens* 1520725 with resistance to *Septoria apiicola* as described herein was deposited at the NCIMB (National Collections of Industrial, Food and Marine Bacteria (NCIMB), NCIMB Limited, Ferguson Building; Craibstone Estate, Bucksburn Aberdeen, Scotland, AB21 9YA United Kingdom) on Jan. 6, 2017 under number NCIMB 42711.

REFERENCE

1. Plant Cell, Tissue and Organ Culture: 39, (3) 203-210 (1994)

The invention claimed is:

1. An *Apium graveolens* plant comprising in its genome one or more genomic DNA segments that confer resistance against the plant pathogen *Septoria apiicola*, wherein said plant is grown from a seed deposited under NCIMB Accession No. 42711.

2. A seed or plant part of the plant according to claim 1, wherein the seed or plant part comprises in its genome the one or more genomic DNA segments that confer resistance against the plant pathogen *Septoria apiicola* present in deposit NCIMB 42711.

3. An *Apium graveolens* seed deposited under NCIMB Accession No. 42711, wherein said seed comprises in its genome a genomic DNA segment that confers resistance against the plant pathogen *Septoria apiicola*.

* * * * *